United States Patent [19]

Sawa

[11] 4,402,325
[45] Sep. 6, 1983

[54] OPHTHALMIC DEVICE TO DIAGNOSE THE EYE FUNDUS

[75] Inventor: Seija Sawa, Sakai, Japan

[73] Assignee: Minolta Camera Kabushiki Kaisha, Osaka, Japan

[21] Appl. No.: 186,669

[22] Filed: Sep. 12, 1980

[30] Foreign Application Priority Data

Sep. 29, 1979 [JP] Japan .................. 54-126006

[51] Int. Cl.³ .................................. A61B 3/00
[52] U.S. Cl. ........................... 128/666; 128/691; 351/7; 351/210
[58] Field of Search ................. 128/664–666, 128/691, 745, 637, 645, 649–650, 652, 297, 6, 676; 351/6–7; 354/62–63

[56] References Cited

U.S. PATENT DOCUMENTS

| | | | |
|---|---|---|---|
| 3,016,000 | 1/1962 | Noyori | 354/62 |
| 3,308,810 | 3/1967 | Galin | 128/676 |
| 3,862,627 | 1/1975 | Hans | 128/643 |
| 3,903,871 | 9/1975 | Chisum et al. | 351/6 |
| 3,925,793 | 12/1975 | Matsumura et al. | 354/62 |
| 3,929,124 | 12/1975 | Yablonski et al. | 351/6 |
| 3,936,844 | 2/1976 | Matsumura | 354/62 |
| 3,948,248 | 4/1976 | Zuckerman | 128/2 T |
| 4,068,932 | 1/1978 | Ohta | 351/7 |
| 4,157,708 | 6/1979 | Imura | 128/666 |
| 4,265,519 | 5/1981 | Pomerantzeff | 351/7 |
| 4,282,882 | 8/1981 | Langham | 128/676 |

FOREIGN PATENT DOCUMENTS 1127947 12/1956 France .................. 351/7
4952395 10/1972 Japan .

OTHER PUBLICATIONS

Weast, Robert C., *CRC Handbook of Chem. and Phy.*, 52nd Edition, 1971-1972, p. E-186.

*Primary Examiner*—Kyle L. Howell
*Assistant Examiner*—Max F. Hindenburg
*Attorney, Agent, or Firm*—Jackson, Jones & Price

[57] ABSTRACT

The present invention provides an ophthalmic device to diagnose the circulation of blood in an eye fundus by producing a pair of plethysmograms for synchronized comparison. A pair of fiber optic conduits are attached to a coupler that can be sealingly affixed to the exterior surface of the cornea of an eye. The coupler can be attached to the exterior surface of the eye by the application of subatmospheric pressure within the coupler. Light is introduced on the axis of the pupil through a central light exit region that is physically small enough relative to a dilated pupil to prevent the reflection of light from the iris. The light reflected from the eye fundus is received in a peripheral light receiving region. The light signals are converted into electrical voltage levels that are ultimately used to produce a visual display of the plethysmograms.

16 Claims, 6 Drawing Figures

OPHTHALMIC DEVICE TO DIAGNOSE THE EYE FUNDUS

BACKGROUND OF THE INVENTION

1. Field of the Invention

The present invention relates to an ophthalmic medical device and more prticularly, to an apparatus for diagnosing diseases through non-invasive measurement of the eye fundus.

2. Description of the Prior Art

Considerable advances have occurred in the practice of ophthalmic medicine in recent years, for example, laser treatment of the retina of an eye has become common. To assist the ophthalmic medical profession in examining a patient's eye and diagnosing various diseases, various forms of eye fundus cameras have been utilized. One of the causes of loss of human eyesight is diabetic retinopathy. This diabetic condition affects the small eye blood vessels by increasing their size. Frequently, these blood vessels will break due to their fragility and will result in a destruction of the optic rod and cone receptors of the retina resulting from a lack of nutrition by blood flow. When this disease has been properly diagnosed, the medical profession has been able to retard the loss of eyesight by burning or searing closed the specific enlarged blood vessels with the use of a laser. The localized loss of receptors in the burnt area does not reduce the overall vision.

The conventional manner in which a diabetic retionopathy is diagnosed is by use of an eye fundus camera. The doctor aligns the patient with his chin on a headrest and centers the camera optics relative to the patient's eye. Frequently, flash illumination is utilized for taking photographs. The doctor subsequently makes his diagnostic decision by observing the photographs taken of the eye fundus. This diagnosis, however, depends greatly on the personal ability and experience of the doctor. Accordingly, a reliable diagnosis is only possible by a highly skilled doctor and the subjective possibility of the wrong diagnosis is an inherent problem.

U.S. Pat. Nos. 4,068,932, 3,936,844, 3,925,793 and 3,016,000, plus French Pat. No. 1,127,947 (1956) are cited of general interest to disclose various eye fundus cameras. U.S. Pat. No. 3,948,248 is cited of general interest to disclose a central transmission of ultrasonic energy with a concentric pickup device surrounding the oscillating transducer.

Finally, U.S. Pat. No. 4,157,708 is cited of general interest to disclose the obtaining of a final plethysmograph that is free from any noise resulting from eye cornea reflection as a result of a subtractive processing of a first and second output signal from different wavelengths.

The ophthalmic medical profession is still seeking an optimum medical apparatus to diagnose diseases from measurements of the eye fundus.

SUMMARY OF THE INVENTION

An object of the present invention is to provide a novel ophthalmic device that permits an easy and objective diagnosis of an eye fundus condition while minimizing the subjective personal skill of the doctor.

Another object of the present invention is to provide an ophthalmic device wherein an output signal having a relatively high signal to noise ratio can be obtained under a stabilized condition.

A further object of the present invention is to provide a novel ophthalmic instrument wherein sufficient illuminating light is introduced into the patient's eye with minimal noise occurring by light being reflected from the iris.

A still further object of the present invention is to provide an ophthalmic device wherein eye measurement is possible irregardless of the subjective movement of the patient's eye.

The present invention includes a source of light capable of introducing at least a bandwidth of energy from the visible to the infrared spectrum. A pair of fiber optic conduits are attached to a coupler that can be sealingly affixed to the exterior surface of the eye. The coupler can be held to the eye by the creation of a subatmospheric pressure in a cavity djacent the exterior of the eye cornea with the coupler being further flexibly mounted to accommodate the minute eye movements. A central fiber optic or light guide is located adjacent the cornea of the eye and aligned with an axis transverse to and extending approximately through the center of the pupil. A peripheral light receiving member is concentrically arranged about the central light guide. The specific dimensions of the light guide members are such that the diameter of the periphery of the light receiving member is less than the conventional dilation of a pupil subject to a mydriatic. The light reflected from the fundus of the eye will be relatively free from any reflection from the iris and will be capable of generating a pair of plethysmograms, one of which will represent a plot from a visible wavelength of light while the second one will represent a plot from at least a near infrared wavelength band of light. The generation of these plethysmograms will be synchronized for subsequent processing and evaluation, so that any variation in amplitude and phase can be utilized to diagnose a condition of the eye.

The features of the present invention which are believed to be novel are set forth in particularity in the appended claims. The present invention, both as to its organization and manner of operation, together with further objects and advantages thereof, may best be understood by reference to the following description, taken in connection with the accompanying drawings.

DETAILED DESCRIPTION OF THE PREFERRED EMBODIMENT

The following specification, taken in conjunction with the drawings, sets forth the preferred embodiments of the present invention in such a manner that any person skilled in the optical and medical fields can utilize the invention. The embodiments of the invention disclosed herein are the best modes contemplated by the inventor in carrying out his invention in a commercial environment, although it should be understood that various modifications can be accomplished within the parameters of this invention.

The human eye is enclosed by three membranes. The uppermost one consists of the transparent cornea, forming the outer bulge, and the opaque sclera enclosing the remainder of the eyeball. The choroid coat contains many nerves and blood vessels and is immediately under the sclera. The innermost membrane of the eye is the retina which lines all the posterior wall of the fundus. Behind the cornea is the iris and the crystalline lens. Muscles in the eye change the size of the pupil for opening an aperture to the lens and other muscles change the shape of the crystalline lens to permit focusing. Two chambers, one anterior to the lens and the other posterior, are filled with transparent material. The first with aqueous humor and the second with the vitreous humor. The aqueous humor has a water consistency similar to blood plasma while the vitreous humor is jelly-like. Although the retina includes blood vessels, the major blood supply of the eye is the choroid layer. Light rays directed towards an eye can experience reflection from the cornea, the fundus and even the iris. In generating a plethysmogram from the fundus of the eye, it is known that the intensity of the reflected light from the fundus will vary due to a pulsation of blood through the blood vessels distributed throughout the fundus, such as in the choroid layer. Additionally, the eye itself is constantly seeking to accommodate ambient light and the eyeball will tremble in minute movements, even when a patient is apparently steadily looking at a point object. This minute trembling of the eyeball can result in irregular variations in the light rays which are reflected from the eye to produce a resultant disturbing noise in the reflected light signal. Generally, the eyeball movements are in the order of 30 to 100 Hz.

Figure 1:
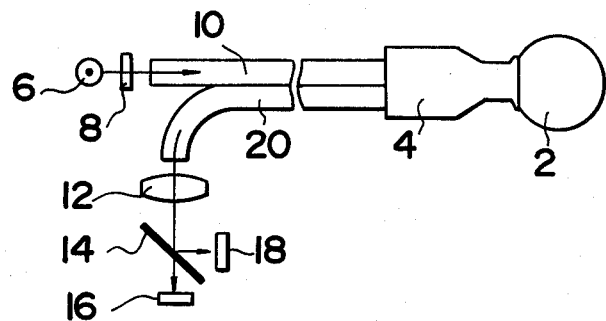
FIG. 1 is a schematic illustration of one embodiment of the present invention.

Referring to FIG. 1, a schematic view of one embodiment of the present invention is disclosed. In FIG. 1, a pickup module 4 is in direct contact with the exterior cornea of the eyeball 2. The cornea contacting area can be formed from a plastic such as polyacetal that is capable of being repetitively sterilized. The configuration of the opening aperture of the pickup module 4 is complimentary to the exterior configuration of the cornea. A light source 6, for example a tungsten lamp or the like, is appropriately mounted and energized to direct light through a band pass filter 8 having the capacity of transmitting a wavelength band between 550 to 1000 m$\mu$. As can be appreciated, a plurality of filters could be used to provide the same desired transmission band.

A fiber optic light guide or conduit 10 carries the light rays from the light source to the pickup module 4 and transmits them into the eye 2. A second fiber optical light guide 20 can receive the reflected light from the eye fundus and transmit it for subsequent processing. A condenser lens 12 can be mounted adjacent an end of the light guide 20 for focusing the light rays on a dichroic mirror 14. A first light sensing device 16 and a second light sensing device 18, such as photodetectors, are aligned with the dichroic mirror 14. The dichroic mirror 14 has the capability of transmitting a critical wavelength of approximately 650 to 700 m$\mu$, while the second light sensing device 18 receives near infrared light of wavelengths 700 to 1000 m$\mu$. As can be appreciated, the dichroic mirror 14 can be replaced by a semitransparent mirror if a pair of interference filters having corresponding transmitting wavelengths are located in front of respectively the first and second light receiving devices 16 and 18.

Figure 2:
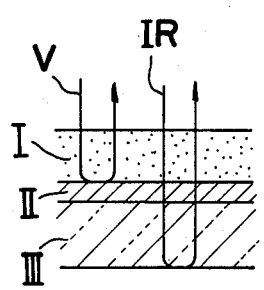
FIG. 2 is a schematic drawing of a cross sectional model of the eye fundus.

FIG. 2 is a schematic cross sectional model of a portion of an eye fundus disclosing the retinal layer I, the pigmented epithelium layer II, and the choroidal layer III, respectively. A light ray from the visible spectrum, V, for example 550 to 650 m$\mu$, is transmitted through the retinal layer I and reflected back from the pigmented epithelium layer II. The near infrared light rays, IR, are transmitted through each of the respective layers before they are reflected back. Therefore, the visible light, V, which is reflected from the eye fundus and enters the first light sensing device 16, will carry with it information relating to the circulation of blood in the retinal layer I. The near infrared light, IR, reflected from the eye fundus and sensed by the second light sensing device 18, will carry information relating to the circulation of blood in the choroidal layer III.

Figure 3:
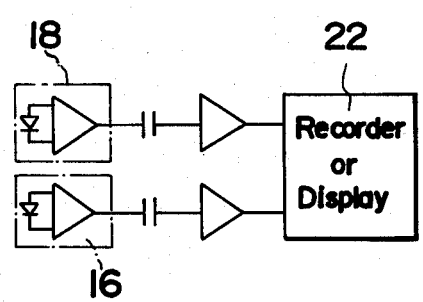
FIG. 3 represents a schematic circuit diagram of a portion of the present invention.

FIG. 3 is a schematic circuit diagram that has been simplified to disclose the broad operation of the electrical circuit of the present invention. Basically, light transducers or sensors convert the time varying intensities of light received by each of the light sensing devices 16 and 18 into corresponding voltage signals which can be amplified nd filtered to drive a recorder or display device. Each of the light sensing devices 16 and 18 will generate a respective plethysmogram which can be synchronized with conventional techniques.

A pen recorder 22 or the like can record synchronously on a piece of paper the pair of plethysmographs respectively of visible and near infrared light rays to permit a synchronized comparison between the pair of plethsymographs. Alternatively, an oscilloscope display or the like can be used to display synchronously on a screen the pair of plethysmographs to permit a direct observation and comparison of the synchronized wave forms of these plethysmographs.

Figure 4:
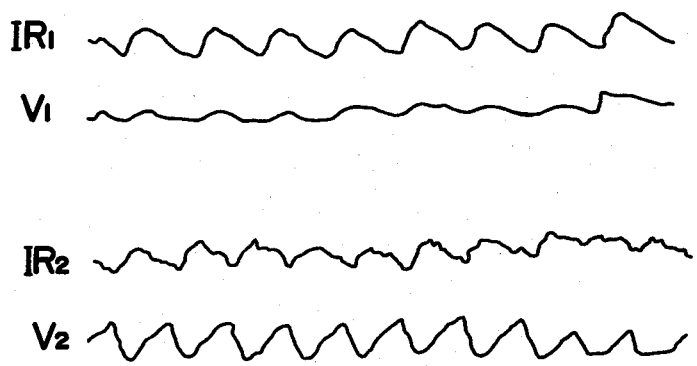
FIG. 4 represents graphical plots of actual clinical examinations with the present invention.

FIG. 4 discloses actual examples of a clinical examination by means of the present invention. In FIG. 4, $IR_1$ and $V_1$ are a pair of synchronized plethysmograms for, respectively, the near infrared light rays and the visible light rays for a first patient, while $IR_2$ and $V_2$ are similar synchronized plethysmograms for a second patient. The medical diagnosis was that the first patient was normal while the second patient was suffering from diabetic retinopathy. As can be seen, the plethysmograms $IR_1$ and $V_1$ for the first patient have wave forms that are substantially similar, although the amplitudes differ from each other. Referring to the second set of plethysmograms, $IR_2$ and $V_2$, the wave form of $V_2$ is almost 180 degrees out of phase or inverted in comparison with that of $IR_2$. This variance in the wave form or phase of the wave of the plethysmogram for the visible ray as compared to the synchronized plethysmogram for the near infrared ray provides an objective diagnosis of the diabetic retinopathy of the eye. Other diseases than diabetic retinopathy such as black out or macular hale can be detected by a synchronized comparison of plethysmograms which are created by visible rays and near infrared rays, respectively.

Figure 5:
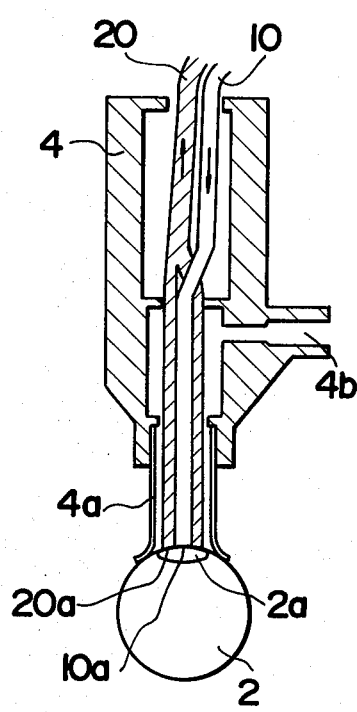
FIG. 5 is a cross sectional view of the pickup module of the present invention.
Figure 6:
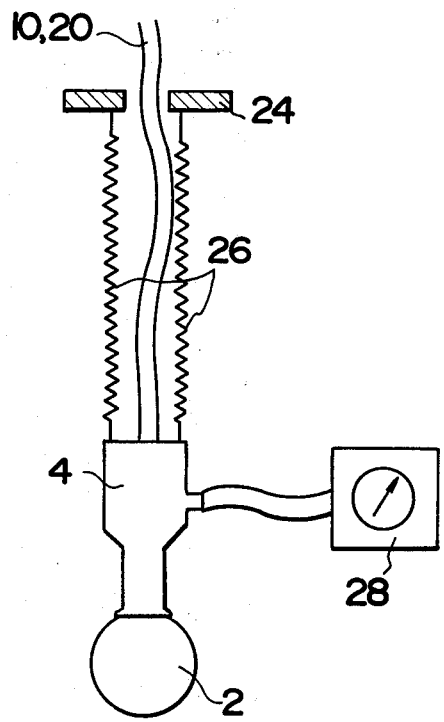
FIG. 6 represents a cross sectional view of a flexible coupling attached to the pickup module of the present invention.

FIGS. 5 and 6 disclose schematic illustrations of the pickup module of the present invention and the manner in which it can be mounted in order to receive a light signal of a high S/N under stabilized conditions. As is appreciated, it is very difficult to obtain from the eye fundus an optical signal of a high S/N under a stabilized condition since the reflecting power of the eye fundus is relatively low and the illumination of the eye fundus and the picking up of the reflected light therefrom are limited by the narrow aperture of the pupil of the iris.

Generally, the patient will receive a mydriatic drug to dilate the pupil prior to any light measurement of the eye. The actual dilation of a pupil will vary depending upon the age of the patient, and even upon the color of the patient's eye. Generally, a dilated pupil will have a diameter in the range of 10 mm to 7 mm.

The conventional technique of using an eye fundus camera is to illuminate the eye from light transmitted through the peripheral edge of the pupil with the reflected light being picked up through the central area of the pupil. The reason for this particular arrangement is to ensure that the transmission of the most significant light containing the information, that is, the reflected light, will occur through the center of the pupil wherein the optical condition is best and the amount of undesirable reflection can be minimized.

The use of an optical fiber to introduce illuminating light into the eye will produce a light pencil emerging from the end of the optical fiber that will be divergent within a considerable angle. Therefore, even if the diameter of the light exit is less than that of the pupil dilated by the mydriatic drug, a portion of the illuminating light will extend beyond the pupil and inevitably impinge on the iris with corresponding reflection to create significant intensity of signal noise. Attempts to decrease the diameter of the light exit, however, will be unfavorable to the projection of a necessary and sufficient amount of illuminating light.

The present invention does not attempt to utilize the conventional use of peripheral illuminating light, but instead mounts the light transmitting fiber optic 10 so that its light exit area 10a is aligned with an axis transverse to and extending approximately through the center of the pupil of the eye. The light receiving fiber optic guide 20, as shown in FIG. 5, is mounted so that its light receiving or entrance portion 20a is located concentrically around the peripheral area of the light exit 10a. The radius of the periphery of the light entrance 20a is less than the radius of the pupil 2a of the eye when dilated by the mydriatic drug. By adopting this particular arrangement, the restrictive aperture of pupil 2a is then most effectively utilized. The physical dimensions of the combined light exit 10a and light entrance 20a is approximately equal to the area of the pupil 2a in the mydriatic condition. The diameter of the periphery of the light exit 10a is sufficiently less than that of the mydriatic pupil 2a by the corresponding width of the ring-shaped light entrance 2a that surrounds light exit 10a. As a result of this configuration, the light exit 10a is sufficiently small so that all the light emerging from light exit 10a will pass through the pupil 2a even though the emerging light pencil will be divergent. As a result, the noise which would be caused by reflection from the iris is avoided, and the illumination of the eye fundus is increased. Additionally, by mounting the light exit 10a and light entrance 20a immediately adjacent the exterior surface of the cornea, reflection from the cornea will not be a significant problem.

To eliminate the creation of noise from the minute eye movement, the pickup module 4 includes a pliable exterior tube 4a that surrounds and is spaced from the fiber optic members. The relative dimensions of the end of the tube 4a, light exit 10a, and light entrance 20a are capable of being in contact with the exterior surface of the cornea. The tube 4a is spaced from the fiber optics and that space along with a connecting manifold can be attached to a pump 28 that also can include an output gauge for monitoring the reduction in air pressure to provide a subatmospheric suction for holding the tube 2a against the cornea of the eye.

Complementing this suction connection of the eye module pickup 4 to the eyeball 2 is a flexible mounting or suspension member disclosed in FIG. 6. Thus, the module pickup 4 can be loosely supported by a spring 26 suspended from a fixed base 24, thereby preventing the weight of the pickup module 4 from pressing against the cornea and for allowing substantially free movement of the pickup module 4 to follow minute motions of the eyeball 2. By carefully controlling the relative displacement and spring forces utilized, the module pickup 4 can be rendered substantially weightless relative to the eye while adhering to the cornea of the eye, will not burden the eyeball with any additional pressure, and will become substantially one with the movement of the eyeball. As a result of this arrangement, the light signals that are obtainable for generating the plethysmograms will come from a stabilized eye condition irregardless of any movement of the patient or his eye. As a result of this novel arrangement, any efforts to manually press the pickup module 4 on the patient's eye will not be necessary and the relative position of the pickup module 4 to that of the pupil will be maintained and thereby will eliminate any potential sources of errors to create a noise in the resultant signal.

Accordingly, a non-invasive ophthalmic apparatus for measuring the eye is provided that not only facilitates the positioning of the measuring eye module relative to the eye, but further holds the module on the eye with substamospheric pressure. Accordingly, an easy measurement and generation of a pair of plethysmograms that can be synchronized for diagnosis is possible without inflicting any substantial discomfort or pain on the patient.

As can be appreciated by a person skilled in this field, variations of the present invention can be accomplished and accordingly, the scope of the present invention should be measured solely from the following claims.

What is claimed is:

1. An opthalmic device for measuring blood circulation in the eye fundus to diagnose the condition of the eye comprising:
   means for generating a source light including wavelengths in at least the visible and near infrared range;
   means for introducing the source light into an eye;
   means for receiving the light reflected from the fundus of the eye;
   first means responsive to a visible wavelength band of light picked up by the receiving means for producing a first electric signal indicative of a first plethysmogram;
   second means responsive to a near infrared wavelength band of light picked up by the receiving means for producing a second electric signal indicative of a second plethysmogram; and
   means responsive to the first and second electric signals for visually presenting waveforms of the individual first and second plethysmograms to provide a synchronized comparison therebetween, whereby diagnosis of the eye is possible as a result of the synchronized comparison between the visually and individually presented waveforms of the first and second plethysmograms.

2. The invention of claim 1, further comprising means for transmitting the visible wavelength band of light picked up by the receiving means to the first producing means and for transmitting the near infrared wavelength band of light picked up by the receiving means to the second producing means.

3. The invention of claim 2, wherein the visible wavelength band is defined between 550 to 600 mµ while the near infrared wavelength band is defined between 700 to 1000 mµ by the transmitting means.

4. The invention of claim 1 wherein the means for presenting the waveforms comprises means connected to the first and second producing means for synchronously and individually recording on paper the first and second plethysmograms.

5. The invention of claim 1 wherein the means for presenting the waveforms comprises means connected to the first and second mens for synchronously and individually displaying the first and second plethysmograms.

6. The invention of claim 1, wherein the introducing means comprises a light exit, and the receiving means comprises a light entrance concentrically arranged around the light exit, the radius of the periphery of the light entrance is less than the normal radius of the pupil of an eye dilated by a mydriatic.

7. The invention of claim 6, further comprising means for adhering the light exit and light entrance to the front of the eye and means for flexibly supporting the light exit and light entrance to allow free motion thereof to follow movement of the eyeball.

8. The invention of claim 7, wherein the adhering means comprises a tube arranged around the light entrance with a gap formed therebetween and means for removing the air in a space enclosed by the eye front, the tube and the light entrance.

9. An opthalmic device for a novel diagnosis method by means of measuring the blood circulation in the eye fundus comprising:
first means for photoelectrically obtaining a first plethysmogram from an eye fundus with respect to visible light in the wavelength band of 550 to 650 mµ;
second means for photoelectrically obtaining a second plethysmogram from the eye fundus with respect to near infrared light in the wavelength band of 700 to 1000 mµ; and
means for realizing a synchronized comparison of the relative phase and amplitude of the first and second plethysmograms, whereby diagnosis is possible as a result of the comparison.

10. An opthalmic device for measuring blood circulation in the eye fundus to diagnose the condition of the eye and patient comprising:
a source light for generating wavelengths in at least the bandwidth of 550 to 1000 mµ;
an optical system for directing the source light into the eye, and receiving the light reflected from the fundus of the eye;
a first light sensing device connected to the optical system for providing a first continuous plethysmogram signal of reflected light representative of a wavelength band within the range of 550 to 700 mµ;
a second light sensing device connected to the optical system for providing a second continuous plethysmogram signal of reflected light representative of the wavelength band within the range of 700 to 1000 mµ; and
means for synchronizing the first and second continuous plethysmogram signals to permit a comparison of the phase and amplitude of the respective plethysmograms whereby their relative values can be compared with predetermined known values to diagnose the condition of the eye and patient.

11. The invention of claim 10 wherein the optical system includes a light exit member capable of being located adjacent an optical axis of an eye surface for projecting the source light into and through a dilated eye pupil without reflection from the iris and a light entrance member capable of being located adjacent and off the optical axis of the eye for receiving the light reflected from the fundus of the eye.

12. The invention of claim 11 further including means for flexibly supporting the optical system adjacent and in contact with the eye to allow substantially free movement of the optical system to track the minute motion of the patients' eye and thereby substantially eliminate the introduction of signal noise from eye movements in the resulting plethysmograms.

13. The invention of claim 12 further including means for adhering the optical system to the eye surface.

14. A noninvasive opthalmic apparatus for facilitating measurement of an eye comprising:
means for measuring a property of an eye including a light source, a first light guide for directing light into the eye having a light exit region located adjacent the cornea of the eye and aligned with an axis of the pupil transverse to and extending approximately through the center of the pupil of the eye, a second light guide for receiving light reflected from the eye having a light entrance region offset from the axis of the pupil and means for monitoring the reflected light;
means for providing a sealing contact to the exterior surface of the eye to facilitate positioning of the light exit and entrance regions relative to the eye;
means for providing a subatmospheric pressure to the surface of the eye to maintain an operative position of the light exit and entrance regions and the eye; and
means for flexibly supporting the light exit and entrance regions to permit free movement thereof to substantially follow any physical motion of the eye.

15. The invention of claim 14 wherein the light entrance region is concentrically arranged about the light exit region, the radius of the periphery of the light entrance is less than the radius of a conventional dilated pupil subject to measurement.

16. An opthalmic device for measuring the blood circulation in the eye fundus to diagnose the condition of the eye, comprising:
means for generating a source light;
a light exit capable of location adjacent an eye surface for projecting the source light from the generating means into the eye;
a light entrance capable of location adjacent an eye surface for picking up the light reflected from the fundus of the eye;
means responsive to the light picked up by the light entrance for producing an electric signal indicative of information relating to the blood circulation in the eye fundus, wherein the light entrance is concentrically arranged around the light exit, the radius of the periphery of the light entrance is less than the radius of a normal eye pupil dilated by a mydriatic; and
means for adhering the light exit and light entrance to the eye surface.

* * * * *

UNITED STATES PATENT AND TRADEMARK OFFICE
CERTIFICATE OF CORRECTION

PATENT NO. : 4,402,325
DATED : September 6, 1983
INVENTOR(S) : Seiji Sawa

It is certified that error appears in the above-identified patent and that said Letters Patent are hereby corrected as shown below:

Title page: after "Inventor:" delete "Seija" and insert --Seiji--.

Col 2, line 18, delete "djacent" and insert --adjacent--.

Col 4, line 27, delete "nd" and insert --and--.

Col 7, line 19, delete "mens" and insert --means--.

Signed and Sealed this

Nineteenth Day of June 1984

[SEAL]

Attest:

GERALD J. MOSSINGHOFF

Attesting Officer

Commissioner of Patents and Trademarks